US011662034B2

(12) United States Patent
Albertsen et al.

(10) Patent No.: US 11,662,034 B2
(45) Date of Patent: May 30, 2023

(54) FILTERED VACUUM RELIEF VENT VALVE

(71) Applicant: Quest Medical, Inc., Allen, TX (US)

(72) Inventors: Jeff J. Albertsen, McKinney, TX (US); Kenneth A. Jones, McKinney, TX (US)

(73) Assignee: QUEST MEDICAL, INC., Allen, TX (US)

( * ) Notice: Subject to any disclaimer, the term of this patent is extended or adjusted under 35 U.S.C. 154(b) by 477 days.

(21) Appl. No.: 16/936,963

(22) Filed: Jul. 23, 2020

(65) Prior Publication Data

US 2021/0025509 A1 Jan. 28, 2021

Related U.S. Application Data (60) Provisional application No. 62/877,925, filed on Jul. 24, 2019.

(51) Int. Cl.
*F16K 15/14* (2006.01)
*A61M 39/24* (2006.01)
*A61M 1/36* (2006.01)

(52) U.S. Cl.
CPC ........... *F16K 15/147* (2013.01); *A61M 39/24* (2013.01); *A61M 1/3666* (2013.01); *A61M 2039/242* (2013.01); *A61M 2039/2446* (2013.01); *A61M 2039/2473* (2013.01); *A61M 2205/75* (2013.01)

(58) Field of Classification Search
CPC ... F16K 15/147; A61M 39/24; A61M 1/3666; A61M 2039/242; A61M 2039/2446; A61M 2039/2473; A61M 2205/75
See application file for complete search history.

(56) References Cited

U.S. PATENT DOCUMENTS

| 2,355,862 A | 8/1944 | Harper |
| 2,417,968 A | 3/1947 | Browne |
| 2,662,724 A | 12/1953 | Cut |

(Continued)

FOREIGN PATENT DOCUMENTS

| CN | 201668805 | 12/2010 |
| DE | 2230642 | 12/1972 |

(Continued)

OTHER PUBLICATIONS

Quest Medical, Inc., "Retroguard 4007100," 2018, 1 page.

(Continued)

*Primary Examiner* — Daphne M Barry
*Assistant Examiner* — Frederick D Soski
(74) *Attorney, Agent, or Firm* — Trop, Pruner & Hu, P.C.

(57) ABSTRACT

An embodiment includes a valve comprising: a valve channel that couples a valve input to a valve output; a one-way valve included within the channel; a filter; a first pressure relief port, wherein the first pressure relief port is configured to relieve negative pressure when pressure at the valve output is less than pressure at the valve input; a second pressure relief port, wherein the second pressure relief port is configured to relieve positive pressure when pressure at the valve output is greater than pressure at the valve input; wherein the one-way valve includes a monolithic portion that simultaneously seals the channel, the first pressure relief port, and the second pressure relief port; wherein the filter covers the first pressure relief port.

16 Claims, 5 Drawing Sheets

(56) References Cited

U.S. PATENT DOCUMENTS

| | | | |
|---|---|---|---|
| 3,084,707 A | 4/1963 | Frye | |
| 3,416,557 A | 12/1968 | Schoenecker | |
| 3,508,576 A | 4/1970 | Gross | |
| 3,646,956 A | 3/1972 | Rogers | |
| 3,807,444 A | 4/1974 | Fortune | |
| 3,827,456 A | 8/1974 | Sheppard | |
| 3,896,733 A | 7/1975 | Rosenberg | |
| 3,938,513 A | 2/1976 | Hargest | |
| 4,084,606 A * | 4/1978 | Mittleman | A61M 5/00 137/854 |
| 4,182,355 A | 1/1980 | Briel | |
| 4,215,724 A | 8/1980 | Logsdon | |
| 4,332,249 A | 6/1982 | Joslin | |
| 4,428,392 A | 1/1984 | Jones | |
| 4,449,525 A | 5/1984 | White et al. | |
| 4,475,899 A | 10/1984 | Muller | |
| 4,488,961 A | 12/1984 | Spencer | |
| 4,492,253 A * | 1/1985 | Raftis | F16K 15/147 137/849 |
| 4,502,502 A * | 3/1985 | Krug | A61M 39/24 137/526 |
| 4,514,742 A | 4/1985 | Suga | |
| 4,520,811 A | 6/1985 | White et al. | |
| 4,521,212 A | 6/1985 | Ruschke | |
| 4,524,805 A | 6/1985 | Hoffman | |
| 4,535,819 A * | 8/1985 | Atkinson | F16K 15/147 604/122 |
| 4,624,286 A | 11/1986 | Frohn | |
| 4,642,097 A | 2/1987 | Siposs | |
| 4,671,786 A | 6/1987 | Krug | |
| 4,712,583 A | 12/1987 | Pelmulder | |
| 4,725,266 A | 2/1988 | Siposs | |
| 4,758,224 A | 7/1988 | Siposs | |
| 4,769,012 A | 9/1988 | Quang et al. | |
| 4,890,637 A | 1/1990 | Lamparter | |
| 4,919,167 A * | 4/1990 | Manska | F16K 15/141 137/853 |
| 4,944,732 A * | 7/1990 | Russo | A61M 39/0247 604/105 |
| 4,948,092 A * | 8/1990 | Kasper | F16K 15/147 251/82 |
| 4,966,199 A * | 10/1990 | Ruschke | F16K 15/141 137/843 |
| 5,010,925 A * | 4/1991 | Atkinson | F16K 15/147 137/846 |
| 5,098,405 A * | 3/1992 | Peterson | A61M 39/02 604/246 |
| 5,121,840 A | 6/1992 | Schram | |
| 5,279,550 A | 1/1994 | Habib et al. | |
| 5,301,707 A * | 4/1994 | Hofsteenge | F16K 15/147 137/12 |
| 5,308,333 A | 5/1994 | Skakoon | |
| 5,401,255 A | 3/1995 | Sutherland et al. | |
| 5,575,279 A | 11/1996 | Beplate | |
| 5,634,905 A | 6/1997 | Rudolph | |
| 5,660,205 A * | 8/1997 | Epstein | F16K 15/148 137/853 |
| 5,707,356 A | 1/1998 | Paul | |
| 5,727,594 A | 3/1998 | Choksi | |
| 5,771,935 A | 6/1998 | Myers | |
| 5,954,696 A | 9/1999 | Ryan | |
| 6,044,859 A * | 4/2000 | Davis | F16K 15/147 137/15.19 |
| 6,053,194 A * | 4/2000 | Nelson | F16K 17/14 137/71 |
| 6,053,896 A | 4/2000 | Wilson et al. | |
| 6,099,493 A | 8/2000 | Swisher | |
| 6,105,609 A | 8/2000 | Polidan et al. | |
| 6,136,253 A | 10/2000 | Bennett | |
| 6,142,980 A * | 11/2000 | Schalk | A61M 1/367 604/129 |
| 6,162,354 A | 12/2000 | Yang et al. | |
| 6,240,962 B1 | 6/2001 | Tai | |
| 6,367,505 B1 * | 4/2002 | Raftis | F16K 15/147 137/846 |
| 6,390,130 B1 | 5/2002 | Guala | |
| 6,648,003 B2 | 11/2003 | Weber | |
| 6,691,703 B2 | 2/2004 | Mckinney et al. | |
| 6,851,440 B2 | 2/2005 | Kline | |
| 6,948,521 B2 | 9/2005 | Fukano | |
| 6,968,976 B2 | 11/2005 | Masuda | |
| 7,037,303 B2 * | 5/2006 | Beaufore | A61M 25/04 604/323 |
| 7,097,690 B2 | 8/2006 | Usher et al. | |
| 7,278,981 B2 | 10/2007 | Ellingboe et al. | |
| 7,284,572 B2 | 10/2007 | Kach | |
| 7,287,545 B2 | 10/2007 | Zelson | |
| 7,302,960 B2 * | 12/2007 | Patzer | A61M 39/02 137/12 |
| 7,370,645 B2 | 5/2008 | Freeman | |
| 7,431,050 B2 | 10/2008 | Yamazaki | |
| 7,673,653 B2 | 3/2010 | Mijers et al. | |
| 7,837,658 B2 | 11/2010 | Cote et al. | |
| 7,878,360 B2 | 2/2011 | Takeda | |
| 7,918,217 B2 | 4/2011 | Walz | |
| 7,997,293 B2 | 8/2011 | Ruschke | |
| 8,074,642 B2 * | 12/2011 | Bruce | A61M 16/208 128/200.14 |
| 8,205,640 B2 | 6/2012 | Kawamura | |
| 8,251,099 B2 | 8/2012 | Carmody et al. | |
| 8,256,465 B2 | 9/2012 | Christenson et al. | |
| 8,382,711 B2 | 2/2013 | Dudar et al. | |
| 8,424,562 B2 | 4/2013 | Berglund | |
| 8,870,739 B2 | 10/2014 | Larose et al. | |
| 9,302,091 B2 | 4/2016 | Butterfield et al. | |
| 9,352,086 B2 | 5/2016 | Guala | |
| 9,358,333 B2 | 7/2016 | Trombley et al. | |
| 9,421,354 B2 | 8/2016 | Carmody et al. | |
| 9,651,161 B2 | 5/2017 | Colm et al. | |
| 9,677,677 B2 | 6/2017 | Spanevello | |
| 9,708,099 B2 | 7/2017 | Siu | |
| 9,714,716 B2 | 7/2017 | Cefai | |
| 9,757,307 B2 | 9/2017 | Waller et al. | |
| 10,052,430 B2 | 8/2018 | Wong et al. | |
| 10,253,899 B2 * | 4/2019 | Wang | F16K 1/46 |
| 2001/0037808 A1 * | 11/2001 | Deem | A61F 2/91 128/200.24 |
| 2001/0054448 A1 * | 12/2001 | McFarland | F16K 15/147 137/849 |
| 2003/0089409 A1 | 5/2003 | Morimoto | |
| 2003/0145888 A1 | 8/2003 | Lin | |
| 2004/0112920 A1 | 6/2004 | Felten | |
| 2004/0188541 A1 | 9/2004 | Maruyama | |
| 2005/0072475 A1 | 4/2005 | Seo | |
| 2006/0189945 A1 | 8/2006 | Adams | |
| 2006/0201576 A1 | 9/2006 | Domenig | |
| 2007/0131725 A1 | 6/2007 | Friedman | |
| 2008/0011667 A1 | 1/2008 | Ruschke | |
| 2008/0185061 A1 * | 8/2008 | Fisk | B60H 1/3233 137/846 |
| 2008/0308166 A1 | 12/2008 | Richmond | |
| 2009/0137941 A1 | 5/2009 | Lynch et al. | |
| 2009/0169693 A1 | 7/2009 | Hoffman | |
| 2012/0004623 A1 | 1/2012 | Tumminaro et al. | |
| 2012/0006860 A1 | 1/2012 | Suffa | |
| 2014/0238497 A1 | 8/2014 | Jones et al. | |
| 2015/0202424 A1 * | 7/2015 | Harton | A61M 39/1055 604/248 |
| 2015/0247504 A1 * | 9/2015 | Moorman | F04D 15/0022 417/36 |
| 2016/0032920 A1 | 2/2016 | Hatami | |
| 2016/0228689 A1 * | 8/2016 | Ferguson | A61J 15/0092 |
| 2016/0270446 A1 | 9/2016 | Shenkal et al. | |
| 2016/0346491 A1 | 12/2016 | Shau et al. | |
| 2017/0065811 A1 | 3/2017 | Iwatschenko et al. | |
| 2017/0100532 A1 * | 4/2017 | Wong | A61M 39/24 |
| 2017/0252524 A1 * | 9/2017 | Krüger | F16K 15/147 |
| 2017/0336023 A1 | 11/2017 | Herman et al. | |
| 2018/0036480 A1 | 2/2018 | Riphagen et al. | |
| 2018/0161796 A1 | 6/2018 | Strange et al. | |
| 2019/0162322 A1 * | 5/2019 | Stenz | B60K 15/05 |

(56) References Cited

U.S. PATENT DOCUMENTS

| | | | |
|---|---|---|---|
| 2019/0224468 A1* | 7/2019 | Jones | A61M 39/105 |
| 2020/0263796 A1* | 8/2020 | Veto | F16K 31/1266 |
| 2021/0025509 A1* | 1/2021 | Albertsen | F16K 15/147 |
| 2021/0338996 A1* | 11/2021 | Harder | A61M 39/24 |

FOREIGN PATENT DOCUMENTS

| | | |
|---|---|---|
| DE | 7112099 U | 4/1973 |
| DE | 8805638 | 6/1988 |
| DE | 102005046673 | 2/2007 |
| EP | 0336307 | 3/1989 |
| EP | 0710488 | 5/1996 |
| EP | 1703183 | 9/2006 |
| EP | 2027885 | 2/2009 |
| EP | 2399621 | 7/2016 |
| FR | 1132251 | 3/1957 |
| FR | 2741690 | 1/1998 |
| GB | 510052 | 7/1939 |
| GB | 955471 | 4/1964 |
| GB | 2000685 | 3/1982 |
| JP | S4967781 | 7/1974 |
| JP | 3569378 | 9/1997 |
| JP | 2001-234902 | 8/2001 |
| JP | 2003028328 | 1/2003 |
| KR | 20-0125817 | 10/1998 |
| KR | 101833488 | 3/2018 |
| NL | 6910395 | 1/1970 |
| WO | WO9222467 | 12/1992 |
| WO | WO9508359 | 3/1995 |
| WO | WO0101024 | 1/2001 |
| WO | WO0191829 | 4/2002 |
| WO | WO03066134 | 8/2003 |
| WO | WO2004106788 | 12/2004 |
| WO | WO2006127347 | 11/2006 |
| WO | WO2012080309 | 6/2012 |
| WO | 2014127707 | 8/2014 |
| WO | WO2017217105 | 12/2017 |
| WO | WO2018164859 | 9/2018 |

OTHER PUBLICATIONS

Quest Medical, Inc., "Retroguard 3/8 in. Arterial Safety Valve," 2014, 1 page.
Nordson Medical, "Check Valves," Jul. 6, 2018, 3 pages.
Halkey Roberts, Medical Products, "Pressue Relief/Activated Valves," 2009, 1 page.
LMS, An Aptar Company, "Silicone/Elastomer Seals, Valves, and Other Fluid-Flow Products," 2014, 1 page.
Quest Medical, Inc., "RLV 4103102," 2018, 1 page.
Quest Medical, Inc., "VRV—II 4003103," 2018, 1 page.
Quest Medical, Inc., "VRV—IIC 4003103," 2018, 1 page.
Smart Products, "CheckValves, Pumps and More," 2017, 15 pages.
CardioSmart, "New Blood Thinner Fails to Help Heart Valve Patients," CardioSmart, cardiosmart.org, American College of Cardiology, Sep. 10, 2013, 3 pages.
U.S. Pat. No. 175,145, issued Mar. 21, 1876, inventor William Painter (unable to add to the patent listing above because it is not a 7 digit patent).
DrugWatch, Kristin Compton, "Heater-Cooler Devices," Jun. 29, 2020, 15 pages total.
Plastomatic, "Technical Articles, Introduction to Check Valves," 2019, 4 pages.
International Searching Authority, "Notification of Transmittal of the International Search Report and the Written Opinion of the International Searching Authority," dated Oct. 19, 2020, in International application No. PCT/US2020/043261.

* cited by examiner

FILTERED VACUUM RELIEF VENT VALVE

CROSS-REFERENCE TO RELATED APPLICATION

This application claims priority to U.S. Provisional Patent Application No. 62/877,925 filed on Jul. 24, 2019 and entitled "Filtered Vacuum Relief Vent Valve", the content of which is hereby incorporated by reference.

TECHNICAL FIELD

Embodiments of the invention are in the field of valves and, in particular, cardiopulmonary bypass equipment.

BACKGROUND

In open heart surgery, excess blood may drain into the left ventricle of the heart, in the aortic root, or in the open chest cavity. This can lead to distention of the ventricle or aorta which may lead to complications during the procedure. Providing suction to these areas may drain the blood from these areas to prevent these complications and provide clean, unobstructed views for the practitioner during the procedures. However, providing excessive suction, reverse blood flow back to these areas, or allowing excessive pressure to build in these areas also pose potential complications to the procedure.

Various extracorporeal circuits are utilized to allow for fluid flow, drainage, and to relieve excessive pressure. One-way or check valves are often used to control the direction of fluid flow and to prevent reverse flow. Relief valves are employed to reduce excessive pressures and/or relieve excessive vacuum.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION

Reference will now be made to the drawings wherein like structures may be provided with like suffix reference designations. In order to show the structures of various embodiments more clearly, the drawings included herein are diagrammatic representations of structures. Thus, the actual appearance of the fabricated device, for example in a photo, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical contact with each other and "coupled" may indicate elements co-operate or interact with each other, but they may or may not be in direct physical contact. Phrases such as "comprising at least one of A and B" include situations with A, B, or A and B.

Applicant determined the above-mentioned valves often contain several elements to achieve the various functionality described. Applicant determined these valves may have complicated and unnecessary geometry which can cause flow path obstructions and lead to increased thrombosis and coagulation in the blood circuit which can lead to further complications which includes occluding the valve. Applicant determined these valves may be expensive and complex to produce. Also, Applicant determined such valves do not provide protection from external contaminates (e.g., from aerolization of liquid in a fluid heater/cooler) which may enter the blood through the various vacuum relief vents. (To prevent excessive vacuum, the valves will open the vacuum relief vent to atmosphere to allow external air to be suctioned into the circuit to ensure excessive vacuum does not collapse the ventricle or aorta).

Embodiments, however, address the drawbacks of the above-mentioned valves. An embodiment provides a simple, low cost design which incorporates necessary functionality for valves of this nature as well as protection from external contaminates which may otherwise be introduced into the blood stream during open heart surgery.

An embodiment includes a vacuum relief vent valve to be used in ventricular vent lines, an aortic vent line, auxiliary suction lines used in cardiovascular surgery, or other lines that interface the patient. An embodiment of a filtered vacuum relief valve is comprised of a unidirectional duckbill valve, inlet and outlet housing bodies, and filter media. The duckbill valve portion has a radial flange to cover vacuum vent openings in the inlet body and a cylindrical sleeve which covers pressure relief vents in the outlet body. The vacuum relief valve contains filter media to cover the external side of the vacuum relief vent to filter the air being introduced to the blood stream through the vacuum vent valves.

Various features of an embodiment contribute to solving the above problems as, without limitation, the following: (1) the duckbill valve provides unidirectional flow (with check valve), positive pressure relief, and vacuum relief all in the unique single design, and (2) the filter media provides filtration of external air and potential contaminates through the vacuum relief vents.

An embodiment uses a 0.2 micron pore size for the filter media to prevent and protect against airborne bacteria that may exist in the operating theater. However, other embodiments may include 0.1, 3., 0.5, 0.7 (or combination thereof) pore size. In an embodiment the duckbill is constructed from a flexible, medical grade material (e.g., silicone) to allow for proper functionality.

Embodiments are advantageous over conventional valves because, without limitation, of the following: (1) embodiments provide unidirectional flow (with check valve), positive pressure relief, and vacuum relief all in a single piece duckbill valve design (or limited piece valve design), (2) simpler construction for improved reliability and lower cost, and (3) reduced thrombosis and coagulation of the blood as a result of simplicity.

While many of the vent valve embodiments include a filter, not all embodiments necessarily include a filter. While some embodiments include a monolithic duckbill valve (where the relief valve portion of the valve and the unidirectional flow portion of the valve are monolithic with each other), in other embodiments the two portions may not be monolithic with each other. Still other embodiments are not limited to a duck valve.

In some embodiments the valve is a standalone product. However, another embodiment includes a kit. For example, the kit includes a valve described herein already attached to a vent line. This pre-coupling of the valve and line relieve some of the burden hospitals bare when needing to couple (e.g., via cutting) valves into existing lines. Other kits may couple a valve to other lines not restricted to cardiac perfusion.

In an embodiment the filter portion of the valve does not contact fluid (e.g., blood) that traverses the valve (e.g., duckbill valve). An embodiment does, however, filter air that comes in contact with blood.

A more detailed discussion of various embodiments now follows.

A cardiopulmonary bypass circuit is a complex network of disposable devices, tubing and equipment designed to handle the circulation and oxygenation of blood during cardiopulmonary bypass surgery. Fluid management is critical to the outcome of the procedures so several safety devices are incorporated into the circuit to prevent retrograde (backward) flow, manage pressures and ensure fluid is being distributed where it needs to, when it needs to. Several key components of the circuit include the cardioplegia delivery system, aortic cardioplegia catheters, surgical equipment used for the procedure (aortic punches and retractotape) and a variety of safety valves used throughout the circuit. Embodiments described herein address safety valves. Such safety valves may be used in, for example and without limitation, the following lines of the circuit: aortic root suction line (e.g., a cardioplegia aortic catheter with safety valve integrated into vent line), cardiotomy suction line, left ventricular vent line, a line coupling an arterial filter and bubble trap to an arterial blood gas sensor, and the like.

Applicant determined there is a risk for airborne pathogen exposure to immunocompromised patients in the operating room (OR). This is a direct result from, for example, issues associated with heater-cooler devices used for various purposes in the OR during cardiopulmonary bypass surgery. Heater-cooler devices are devices which use water reservoirs to store and heat or cool water to be pumped through the oxygenator heat exchanger, cardioplegia heat exchanger, and/or patient blankets. If not maintained properly, microbes and bacteria thrive in the water reservoirs. In some heater-cooler devices, the water tanks are not properly sealed. When flowing, water is splashed around inside the device and those bacteria and microbes can become aerosolized. Cooling fans inside the heater-cooler device can then blow the aerosolized bacteria throughout the OR (including into the sterile field). This may lead to patient infections that in turn lead to complications, long-term care or even death that is linked to the airborne microbes distributed by heater-cooler devices.

As a result, Applicant designed embodiments that address devices where air/patient interfaces might exist as a potential site for infection. In some cases, the vacuum relief functionality of the safety valves provides a direct contact point where air is being sucked in from the environment and ultimately mixed with patient blood. Thus, to promote patient safety an embodiment includes a safety valve with a mechanism to prevent airborne bacteria from entering the blood volume through a filtration mechanism incorporated into the valve.

Embodiments have several critical functions during use such as, for example and without limitation: prevent retrograde flow (e.g., via a duckbill valve), provide vacuum relief (e.g., when used on the ventricular vent line, the negative pressure can prevent suction from causing the ventricle to collapse on itself should the negative pressures rise to unsafe levels), provide positive pressure relief (e.g., if the tubing is loaded in backwards in the roller pump and turned on, the positive pressure relief will relieve that pressure before the duckbill is compromised and retrograde flow is experience); provide an air filtration mechanism to filter out airborne bacteria/pathogens present in the OR. Embodiments may be configured with a filter or without a filter and may improve performance for flow and pressure drop.

Figure 1A:
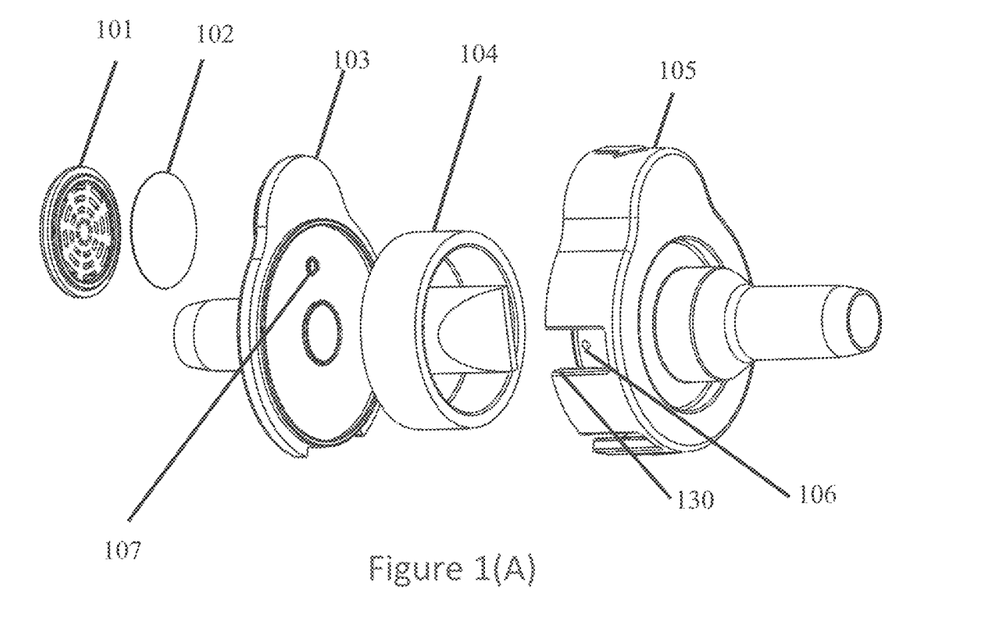
FIGS. 1(A) and 1(B) respectively depict varying angles of exploded views of an embodiment of the invention.
Figure 1B:
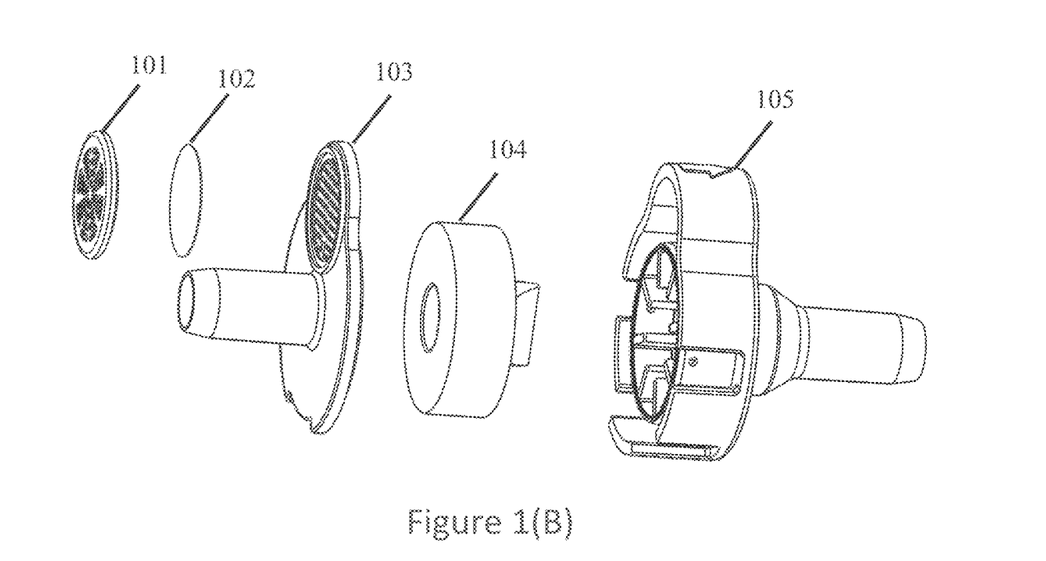

FIGS. 1(A) and 1(B) depict a valve that further comprises filter cover 101, filter media 102, inlet body 103, duckbill valve 104, outlet body 105, pressure relief vent 106, vacuum relief vent 107.

Figure 1C:
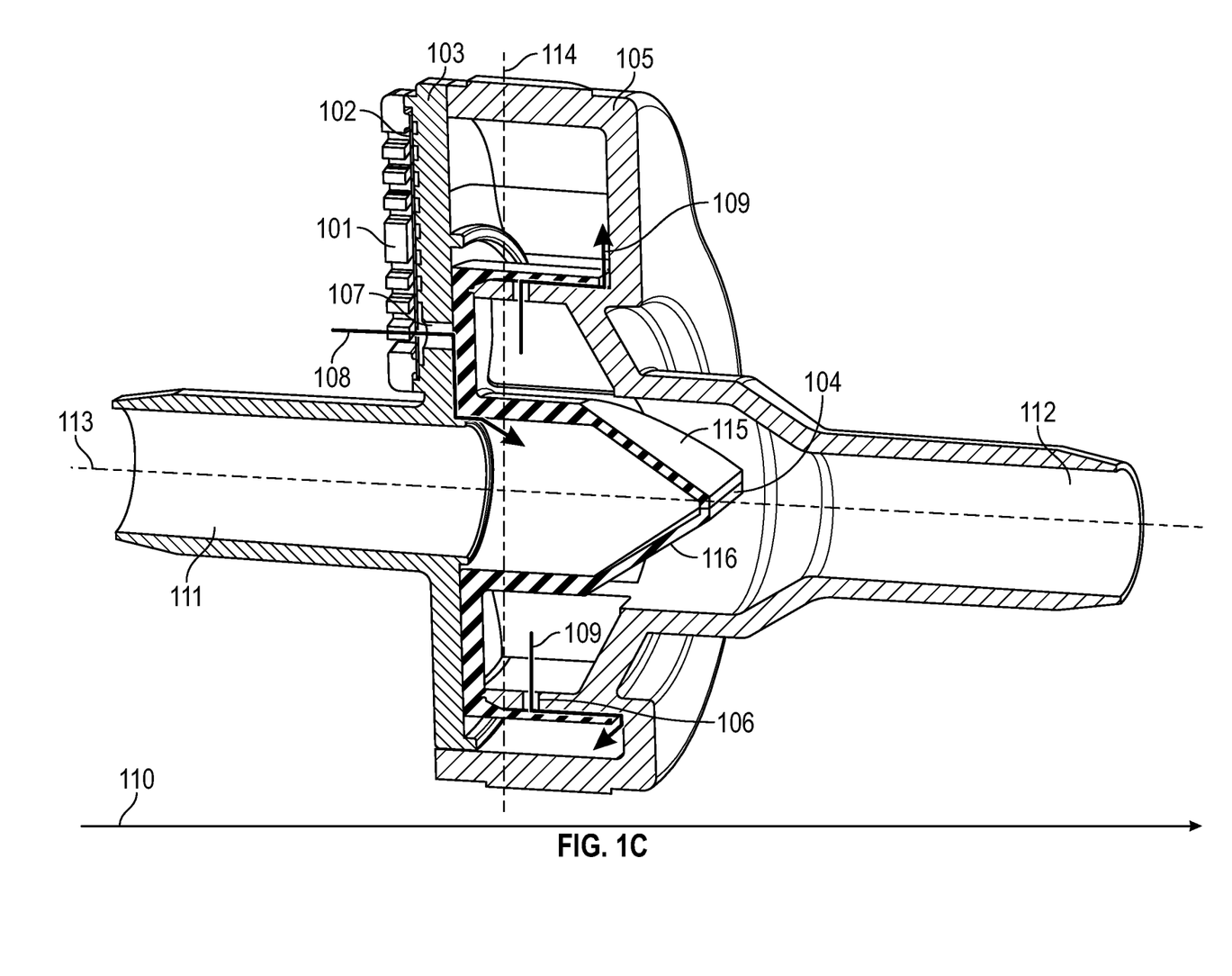
FIG. 1(C) depicts a cross-sectional view of the embodiment.
Figure 1D:
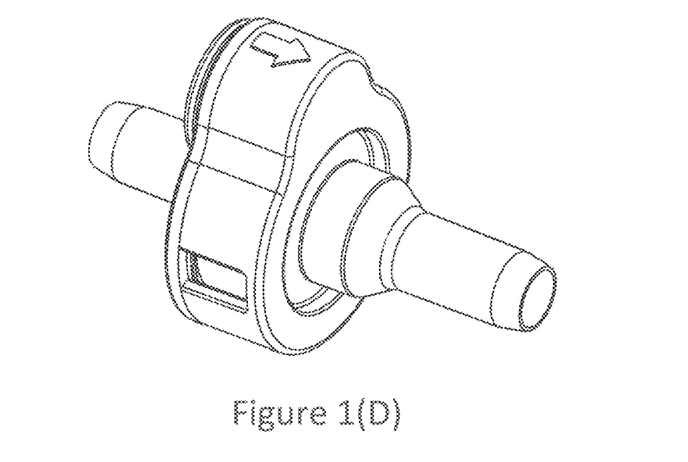
FIGS. 1(D) and 1(E) depict varying angles of assembled views of the embodiment.
Figure 1E:
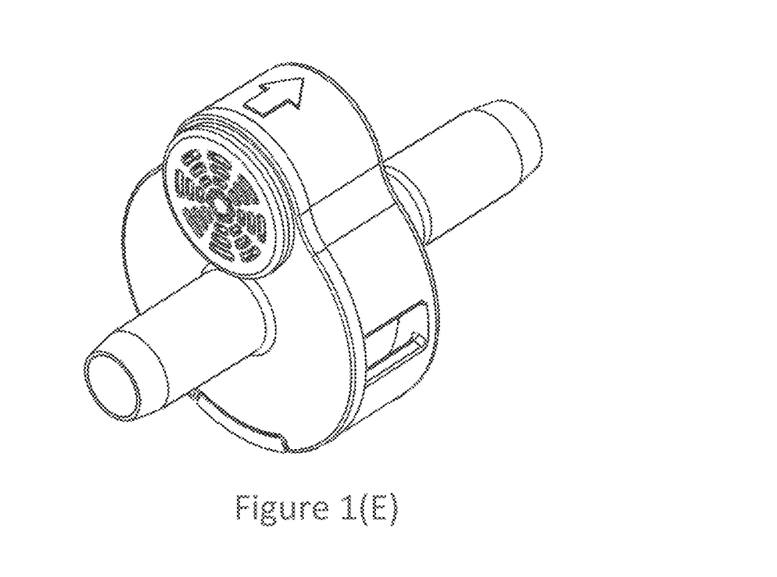

FIG. 1(C) (with unidirectional flow 110 via duckbill valve 104) shows a path 109 for pressure from the output of the channel to be relieved (i.e., positive pressure relief). FIG. 1(A) shows an aperture 130 in the outer housing for the pressure relief and FIG. 1(A) shows an aperture 106 in a wall (see pressure relief vent 106 for pressure relief pathways 109, even though vent 106 is not seen in FIG. 1(C)) that is adjacent the duckbill valve. FIG. 1(C) shows a path 108 for pressure from the input of the channel to be relieved (i.e., vacuum relief pathway 108). For example, if a downstream peristaltic pump (wherein "downstream" is to the right of duckbill valve in FIG. 1(C)) were to create a negative pressure in region 112 the pressure could be alleviated via air traversing along path 108 and across the duckbill valve to region 112. FIG. 1(A) shows an aperture (vacuum relief vent 107) in the housing to facilitate path 108. The aperture is covered by the filter medium 102 and filter cover 101 of FIG. 1(A).

FIG. 1(C) includes a valve that comprises filter cover 101, filter media 102, inlet body 103, duckbill valve 104, outlet body 105, a pressure relief vent (not shown in FIG. 1(C) due to the location where cross-section is taken but the vent is visible (i.e., vent 106) in FIG. 1(A)), and vacuum relief vent 107. Vent 106, if the cross-section of FIG. 1(C) were changed by a small amount, may have an opening at the location of circle 106 of FIG. 1(C). The valve further includes a valve channel that couples a valve input 111 to a valve output 112. Pressure relief port 107 is configured to relieve negative pressure when pressure at the valve output is less than pressure at the valve input. Pressure relief port 106 is configured to relieve positive pressure when pressure at the valve output is greater than pressure at the valve input. Valve 104 includes a monolithic portion that simultaneously seals the channel, pressure relief port 107, and pressure relief port 106. Filter 102 covers the pressure relief port 107. Filter 102 does not cover pressure relief port 106.

The embodiment utilizes a one-way valve (e.g., duckbill valve 104) included within the channel. Valve 104 may include a resilient material, such a silicone. In an alternative embodiment, the one-way valve includes a wagon wheel valve such as the valve of FIG. 2 or 3. The valve of FIG. 2 includes sidewalls 217 that extend generally parallel to axis 213 such that they cover valve 206.

Returning to FIG. 2(C), filter medium 102 is between pressure relief port 107 and cover 101, cover 101 being included in an outermost surface of the valve.

Channel long axis 113 intersects the valve input and the valve output. In an embodiment pressure relief port 107 includes a pressure relief port long axis (not shown) that is parallel to the channel long axis 113. In an embodiment axis 114 is orthogonal to channel long axis 113 and the monolithic portion of valve 104 intersects axis 114 four times. However, in other embodiments the monolithic portion of valve 104 intersects axis 114 at least four times. In an embodiment axis 114 intersects the pressure relief port 106 (not shown in FIG. 1(C)).

Duckbill valve 104 includes two opposing flaps 115, 116 that are biased towards one another in a resting state and that directly contact one another in the resting state. The schematic of FIG. 1(C) does not show the interface between the two flaps (due to abstract high level nature of FIG. 1(C)) wherein such an interface would spread to form a void between the two flaps when the valve is in a non-resting state/active state.

Figure 2:
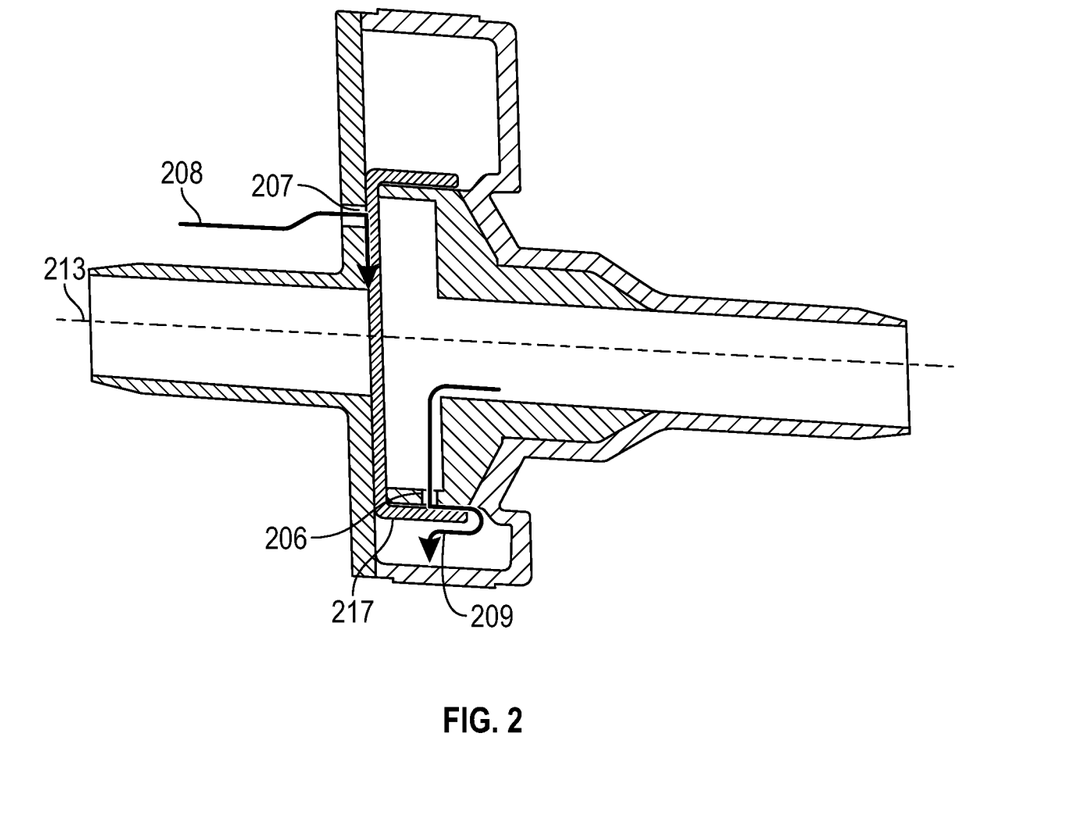
FIG. 2 depicts a cross-sectional view of an embodiment.
Figure 3:
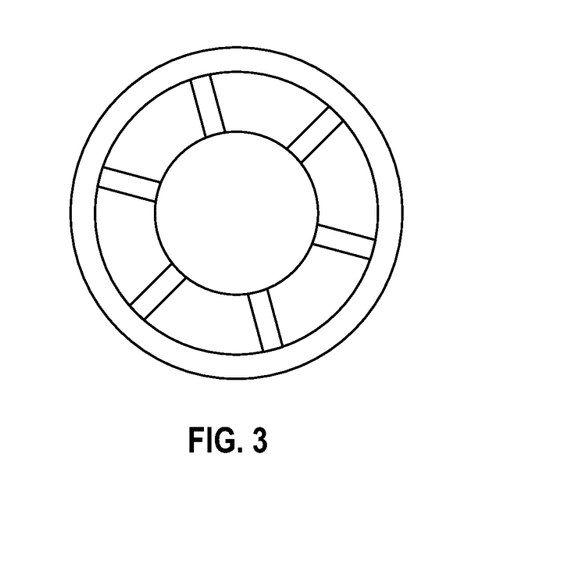
FIG. 3 depicts a frontal view of an embodiment.

FIG. 2 depicts a valve at a perspective that is more abstract and higher level than the perspective of FIG. 1(C). The valve includes the spoke valve of FIG. 3. Note the spoke valve has a sidewall 217 that seals pressure relief vent 206 but not vacuum relief vent 207. FIG. 2 shows a path 209 for pressure from the output of the channel to be relieved (i.e., positive pressure relief) and a path 208 for pressure from the input of the channel to be relieved (i.e., vacuum relief).

Figure 4:
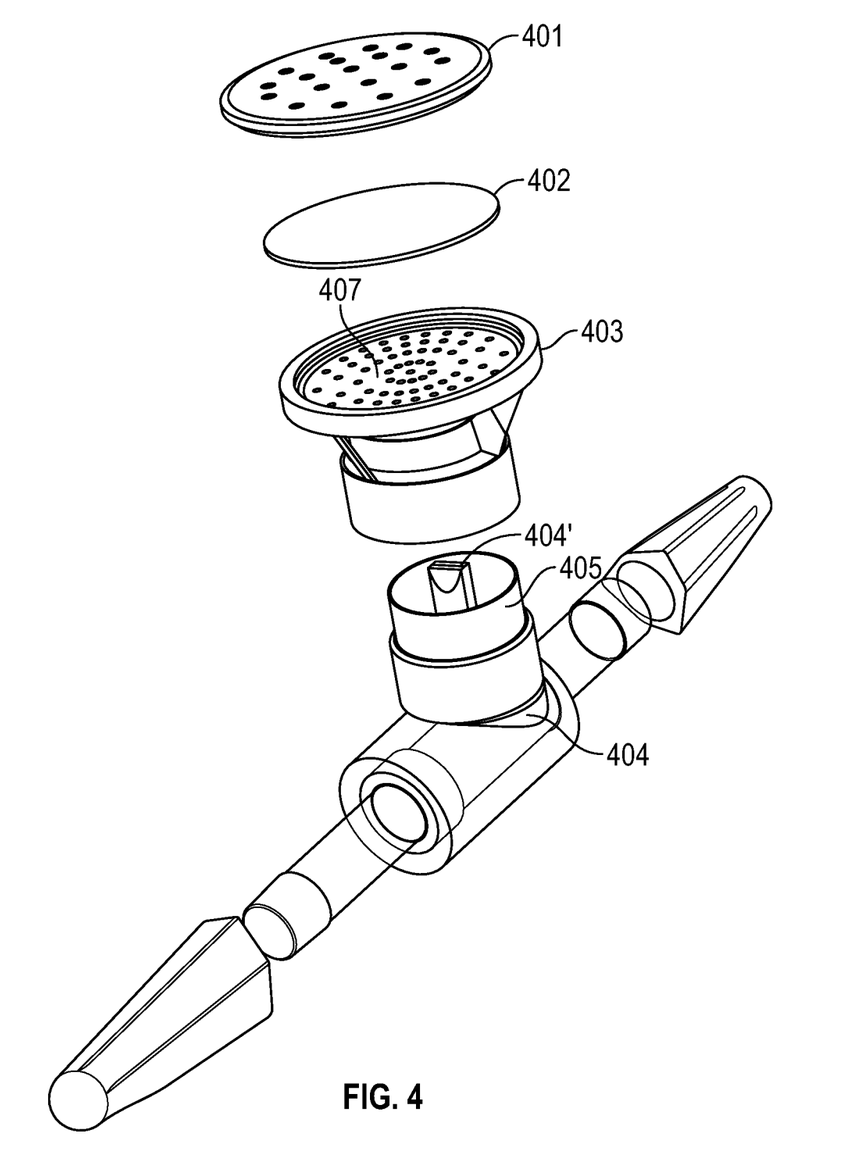
FIG. 4 depicts an exploded view of an embodiment.

FIG. 4 depicts a valve that comprises filter cover 401, filter media 402, inlet body 403, duckbill valve (not shown but located approximately at area 404), duckbill valve 404' (which serves as a pressure relief vent), outlet body 405, and vacuum relief vent 407.

Various examples are now addressed.

Example 1

A valve comprising: a valve channel that couples a valve input to a valve output; a one-way valve included within the channel; a filter; a first pressure relief port, wherein the first pressure relief port is configured to relieve negative pressure when pressure at the valve output is less than pressure at the valve input; a second pressure relief port, wherein the second pressure relief port is configured to relieve positive pressure when pressure at the valve output is greater than pressure at the valve input; wherein the one-way valve includes a monolithic portion that simultaneously seals the channel, the first pressure relief port, and the second pressure relief port; wherein the filter covers the first pressure relief port.

As used herein, "monolithic" means "a single piece". For example, a monolithic portion of a valve may be formed from additive manufacturing (e.g., 3d printing), a mold, two pieces fixedly and permanently coupled to each other via a permanent joint (e.g., weld, adhesive), and the like.

Another Version of Example 1

A valve comprising: a valve channel that couples a valve input to a valve output; a one-way valve included within the channel; a filter; a first pressure relief port, wherein the first pressure relief port is configured to relieve pressure when pressure at the valve output is less than pressure at the valve input; a second pressure relief port, wherein the second pressure relief port is configured to relieve pressure when pressure at the valve output is greater than pressure at the valve input; wherein the one-way valve includes a monolithic portion that simultaneously seals the channel, the first pressure relief port, and the second pressure relief port; wherein the filter covers the first pressure relief port.

Such a valve may be included as a stand-alone valve or in a system of valves of which the valve is just one valve of several valves that cooperate to regulate flow of a fluid (wherein a "fluid" as used herein includes both liquids and gases).

Another Version of Example 1

A valve comprising: a valve channel that couples a valve input to a valve output; a check valve included within the channel; a filter; a first pressure relief port, wherein the first pressure relief port is configured to relieve negative pressure when pressure at the valve output is less than pressure at the valve input; a second pressure relief port, wherein the second pressure relief port is configured to relieve positive pressure when pressure at the valve output is greater than pressure at the valve input; wherein the check valve includes a monolithic portion that simultaneously seals the channel, the first pressure relief port, and the second pressure relief port; wherein the filter covers the first pressure relief port.

A check valve, clack valve, non-return valve, reflux valve, retention valve or one-way valve is a valve that normally allows fluid (liquid or gas) to flow through it in only one direction. A check valve may be a two-port valve, meaning the valve has two openings in the body, one for fluid to enter and the other for fluid to leave.

Another Version of Example 1

A valve comprising: a valve channel that couples a valve input to a valve output; a valve included within the channel; a filter; a first pressure relief port, wherein the first pressure relief port is configured to relieve negative pressure when pressure at the valve output is less than pressure at the valve input; a second pressure relief port, wherein the second pressure relief port is configured to relieve positive pressure when pressure at the valve output is greater than pressure at the valve input; wherein the valve includes a monolithic portion that simultaneously seals the channel, the first pressure relief port, and the second pressure relief port; wherein the filter covers the first pressure relief port.

Example 2

The valve of example 1 wherein the one-way valve includes a resilient material.

Example 3

The valve of example 2 wherein the one-way valve is a duckbill valve.

Example 4

The valve of example 2 wherein the one-way valve is a wagon wheel valve.

Example 5

The valve of example 2 wherein the filter does not cover the second pressure relief port.

Example 6

The valve of example 5 comprising a filter medium and a cover, wherein: the filter medium is between the first pressure relief port and the cover; the cover is included in an outermost surface of the valve.

Example 7

The valve of example 5 wherein: the channel includes a channel long axis that intersects the valve input and the valve output; the first pressure relief port includes a first pressure relief port long axis that is parallel to the channel long axis.

Example 8

The valve of example 5 wherein: the channel includes a channel long axis that intersects the valve input and the valve output; an additional axis is orthogonal to the channel long axis; the monolithic portion intersects the additional axis four times.

Example 9

The valve of example 8 wherein the additional axis intersects the second pressure relief port.

Example 10

The valve of example 5 wherein: the channel includes a channel long axis that intersects the valve input and the valve output; an additional axis is orthogonal to the channel long axis; the monolithic portion intersects the additional axis at least four times.

Example 11

The valve of example 3, wherein: the duckbill valve includes two opposing flaps; the two opposing flaps are biased towards one another in a resting state; the two opposing flaps directly contact one another in the resting state.

Example 12

The valve of example 2 wherein the resilient material includes silicone.

Examples 13-20 are omitted.

Example 21

A valve comprising: a valve channel that couples a valve input to a valve output; a one-way valve included within the channel; a filter; a first pressure relief port, wherein the first pressure relief port is configured to relieve negative pressure when pressure at the valve output is less than pressure at the valve input; a second pressure relief port, wherein the second pressure relief port is configured to relieve positive pressure when pressure at the valve output is greater than pressure at the valve input; wherein the one-way valve is configured to simultaneously seal the channel, the first pressure relief port, and the second pressure relief port; wherein the filter is configured to filter air that passes through the first pressure relief port from outside the valve.

Thus, not all embodiments require the valve to be monolithic.

Another Version of Example 21

A valve comprising: a valve channel that couples a valve input to a valve output; a one-way valve included within the channel; a filter; a first pressure relief port, wherein the first pressure relief port is configured to relieve pressure when pressure at the valve output is less than pressure at the valve input; a second pressure relief port, wherein the second pressure relief port is configured to relieve pressure when pressure at the valve output is greater than pressure at the valve input; wherein the one-way valve is configured to simultaneously seal the channel, the first pressure relief port, and the second pressure relief port; wherein the filter is configured to filter air that passes through the first pressure relief port from outside the valve.

Example 22

The valve of example 21 wherein the one-way valve includes a resilient material.

Example 23

The valve of example 22 wherein the one-way valve is a duckbill valve.

Example 24

The valve of example 22 wherein the one-way valve is a wagon wheel valve.

Example 25

The valve of example 22 wherein the filter does not cover the second pressure relief port.

Example 26

The valve of example 25 comprising a filter medium and a cover, wherein: the filter medium is between the first pressure relief port and the cover; the cover is included in an outermost surface of the valve.

Example 27

The valve of example 25 wherein: the channel includes a channel long axis that intersects the valve input and the valve output; the first pressure relief port includes a first pressure relief port long axis that is parallel to the channel long axis.

Example 28

The valve of example 25 wherein: the channel includes a channel long axis that intersects the valve input and the valve output; an additional axis is orthogonal to the channel long axis; the one-way valve intersects the additional axis four times.

Example 29

The valve of example 28 wherein the additional axis intersects the second pressure relief port.

Example 30

The valve of example 25 wherein: the channel includes a channel long axis that intersects the valve input and the valve output; an additional axis is orthogonal to the channel long axis; the one-way valve intersects the additional axis at least four times.

Example 31

The valve of example 23, wherein: the duckbill valve includes two opposing flaps; the two opposing flaps are biased towards one another in a resting state; the two opposing flaps directly contact one another in the resting state.

Example 32

The valve of example 22 wherein the resilient material includes silicone.

Example 33

The valve of example 22 wherein the one-way valve includes a monolithic portion configured to simultaneously seal the channel, the first pressure relief port, and the second pressure relief port.

Example 34

The valve of example 5 or 15 wherein: the first pressure relief port is configured to be upstream of the one-way valve; the second pressure relief port is configured to be downstream of the one-way valve.

Example 35

The valve of example 5 or 15 wherein: the first pressure relief port is configured to be between the valve input and the one-way valve; the second pressure relief port is configured to be between the valve output and the one-way valve.

Example 36

The valve of example 5 or 15 wherein: the first pressure relief port is configured to fluidly couple to the valve input when (a)(i) pressure at the valve output is less than pressure at the valve input, and (a)(ii) the one-way valve is closed; the second pressure relief port is configured to fluidly couple to the valve output when (b)(i) pressure at the valve output is greater than pressure at the valve input, and (b)(ii) the one-way valve is closed.

Example 37

The valve of example 5 or 15 wherein both of the first and second pressure relief ports directly contact the one-way valve when neither of the first or second pressure relief ports is relieving pressure.

Example 38

The valve of example 5 or 15 wherein: the valve includes an outermost surface; the outermost surface includes a third pressure relief port; the third pressure relief port is configured to relieve pressure when: (a) pressure at the valve output is greater than pressure at the valve input, and (b) the one-way valve is closed.

Example 39

The valve of example 38 wherein: the third pressure relief port is configured to fluidly couple to relieve pressure when: (a) pressure at the valve output is greater than pressure at the valve input, and (b) the one-way valve is closed.

Example 40

The valve of example 1 or 21 comprising: a third pressure relief port, wherein the third pressure relief port is configured to relieve positive pressure when pressure at the valve output is greater than pressure at the valve input; wherein the monolithic portion simultaneously seals the channel, the first pressure relief port, the second pressure relief port, and the third pressure relief port.

For example, note in FIG. 1(C) path 109 is shown to engage valve 104 at two locations (see circles on FIG. 1(C)). Embodiments may have one instance of port 106, two instances of port 106, or more than two instances of port 106.

Example 40

The valve of example 1 or 21 comprising: a third pressure relief port, wherein the third pressure relief port is configured to relieve negative pressure when pressure at the valve output is less than pressure at the valve input; wherein the monolithic portion simultaneously seals the channel, the first pressure relief port, the second pressure relief port, and the third pressure relief port.

Thus, embodiments may allow for more than once instance of port 107.

Example 1a

A valve comprising: a valve channel that couples a valve input to a valve output; a one-way valve included within the channel; a filter; a first pressure relief port, wherein the first pressure relief port is configured to relieve negative pressure when pressure at the valve output is less than pressure at the valve input; a second pressure relief port, wherein the second pressure relief port is configured to relieve positive pressure when pressure at the valve output is greater than pressure at the valve input; wherein the one-way valve includes a monolithic portion that simultaneously seals the channel, the first pressure relief port, and the second pressure relief port; wherein the filter covers the first pressure relief port.

Example 2a

The valve of example 1a wherein the one-way valve includes a resilient material.

Example 3a

The valve according to any of examples 1a-2a wherein the one-way valve is a duckbill valve.

Example 4a

The valve according to any of examples 1a-2a wherein the one-way valve is a wagon wheel valve.

Example 5a

The valve according to any of examples 1a-4a wherein the filter does not cover the second pressure relief port.

Example 6a

The valve according to any of examples 1a-5a comprising a filter medium and a cover, wherein: the filter medium is between the first pressure relief port and the cover; the cover is included in an outermost surface of the valve.

Example 7a

The valve according to any of examples 1a-6a wherein: the channel includes a channel long axis that intersects the valve input and the valve output; the first pressure relief port includes a first pressure relief port long axis that is parallel to the channel long axis.

Example 8a

The valve according to any of examples 1a-6a wherein: the channel includes a channel long axis that intersects the valve input and the valve output; an additional axis is orthogonal to the channel long axis; the monolithic portion intersects the additional axis four times.

Example 9a

The valve of example 8a wherein the additional axis intersects the second pressure relief port.

Example 10a

The valve according to any of examples 1a-6a wherein: the channel includes a channel long axis that intersects the valve input and the valve output; an additional axis is orthogonal to the channel long axis; the monolithic portion intersects the additional axis at least four times.

Example 11a

The valve of example 3a, wherein: the duckbill valve includes two opposing flaps; the two opposing flaps are biased towards one another in a resting state; the two opposing flaps directly contact one another in the resting state.

Example 12a

The valve according to any of examples 2a-11a wherein the resilient material includes silicone.

Examples 13a-20a are omitted.

Example 21a

A valve comprising: a valve channel that couples a valve input to a valve output; a one-way valve included within the channel; a filter; a first pressure relief port, wherein the first pressure relief port is configured to relieve negative pressure when pressure at the valve output is less than pressure at the valve input; a second pressure relief port, wherein the second pressure relief port is configured to relieve positive pressure when pressure at the valve output is greater than pressure at the valve input; wherein the one-way valve is configured to simultaneously seal the channel, the first pressure relief port, and the second pressure relief port; wherein the filter is configured to filter air that passes through the first pressure relief port from outside the valve.

Thus, not all embodiments require the valve to be monolithic.

Example 22a

The valve of example 21a wherein the one-way valve includes a resilient material.

Example 23a

The valve according to any of examples 21a-22a wherein the one-way valve is a duckbill valve.

Example 24a

The valve according to any of examples 21a-22a wherein the one-way valve is a wagon wheel valve.

Example 25a

The valve according to any of examples 21a-24a wherein the filter does not cover the second pressure relief port.

Example 26a

The valve according to any of examples 21a-25a comprising a filter medium and a cover, wherein: the filter medium is between the first pressure relief port and the cover; the cover is included in an outermost surface of the valve.

Example 27a

The valve according to any of example 21a-26a wherein: the channel includes a channel long axis that intersects the valve input and the valve output; the first pressure relief port includes a first pressure relief port long axis that is parallel to the channel long axis.

Example 28a

The valve according to any of example 21a-26a wherein: the channel includes a channel long axis that intersects the valve input and the valve output; an additional axis is orthogonal to the channel long axis; the one-way valve intersects the additional axis four times.

Example 29a

The valve of example 28a wherein the additional axis intersects the second pressure relief port.

Example 30a

The valve according to any of example 21a-26a wherein: the channel includes a channel long axis that intersects the valve input and the valve output; an additional axis is orthogonal to the channel long axis; the one-way valve intersects the additional axis at least four times.

Example 31a

The valve of example 23a, wherein: the duckbill valve includes two opposing flaps; the two opposing flaps are biased towards one another in a resting state; the two opposing flaps directly contact one another in the resting state.

Example 32a

The valve of example 22a wherein the resilient material includes silicone.

Example 33a

The valve according to any of examples 21a-32a wherein the one-way valve includes a monolithic portion configured to simultaneously seal the channel, the first pressure relief port, and the second pressure relief port.

Example 1b

A valve comprising: a valve channel that couples a valve input to a valve output; a one-way valve included within the channel; a filter; a first pressure relief port, wherein the first pressure relief port is configured to relieve negative pressure when pressure at the valve output is less than pressure at the valve input; a second pressure relief port, wherein the second pressure relief port is configured to relieve positive pressure when pressure at the valve output is greater than pressure at the valve input; wherein the one-way valve includes a monolithic portion that simultaneously seals the channel, the first pressure relief port, and the second pressure relief port; wherein the filter covers the first pressure relief port.

Example 2b

The valve of example 1b wherein the one-way valve includes a resilient material.

Example 3b

The valve according to any of examples 1b-2b wherein the one-way valve is a duckbill valve.

Example 4b

The valve according to any of examples 1b-2b wherein the one-way valve is a wagon wheel valve.

Example 5b

The valve according to any of examples 1b-4b wherein the filter does not cover the second pressure relief port.

Example 6b

The valve according to any of examples 1b-4b comprising a filter medium and a cover, wherein: the filter medium is between the first pressure relief port and the cover; the cover is included in an outermost surface of the valve.

Example 7b

The valve according to any of examples 1b-4b wherein: the channel includes a channel long axis that intersects the valve input and the valve output; the first pressure relief port includes a first pressure relief port long axis that is parallel to the channel long axis.

Example 8a

The valve according to any of examples 1b-4b wherein: the channel includes a channel long axis that intersects the valve input and the valve output; an additional axis is orthogonal to the channel long axis; the monolithic portion intersects the additional axis four times.

Example 9b

The valve of example 8b wherein the additional axis intersects the second pressure relief port.

Example 10b

The valve according to any of examples 1b-4b wherein: the channel includes a channel long axis that intersects the valve input and the valve output; an additional axis is orthogonal to the channel long axis; the monolithic portion intersects the additional axis at least four times.

Example 11b

The valve of example 3b, wherein: the duckbill valve includes two opposing flaps; the two opposing flaps are biased towards one another in a resting state; the two opposing flaps directly contact one another in the resting state.

Example 12b

The valve according to any of examples 1b-4b wherein the resilient material includes silicone.
Examples 13b-20b are omitted.

Example 21b

A valve comprising: a valve channel that couples a valve input to a valve output; a one-way valve included within the channel; a filter; a first pressure relief port, wherein the first pressure relief port is configured to relieve negative pressure when pressure at the valve output is less than pressure at the valve input; a second pressure relief port, wherein the second pressure relief port is configured to relieve positive pressure when pressure at the valve output is greater than pressure at the valve input; wherein the one-way valve is configured to simultaneously seal the channel, the first pressure relief port, and the second pressure relief port; wherein the filter is configured to filter air that passes through the first pressure relief port from outside the valve.

Thus, not all embodiments require the valve to be monolithic.

Example 22b

The valve of example 21b wherein the one-way valve includes a resilient material.

Example 23b

The valve according to any of examples 21b-22b wherein the one-way valve is a duckbill valve.

Example 24b

The valve according to any of examples 21b-22b wherein the one-way valve is a wagon wheel valve.

Example 25b

The valve according to any of examples 21b-24b wherein the filter does not cover the second pressure relief port.

Example 26b

The valve according to any of examples 21b-24b comprising a filter medium and a cover, wherein: the filter medium is between the first pressure relief port and the cover; the cover is included in an outermost surface of the valve.

Example 27b

The valve according to any of example 21b-24b wherein: the channel includes a channel long axis that intersects the valve input and the valve output; the first pressure relief port includes a first pressure relief port long axis that is parallel to the channel long axis.

Example 28b

The valve according to any of example 21b-24b wherein: the channel includes a channel long axis that intersects the valve input and the valve output; an additional axis is orthogonal to the channel long axis; the one-way valve intersects the additional axis four times.

Example 29b

The valve of example 28b wherein the additional axis intersects the second pressure relief port.

Example 30b

The valve according to any of example 21b-24b wherein: the channel includes a channel long axis that intersects the valve input and the valve output; an additional axis is orthogonal to the channel long axis; the one-way valve intersects the additional axis at least four times.

Example 31b

The valve of example 23b, wherein: the duckbill valve includes two opposing flaps; the two opposing flaps are biased towards one another in a resting state; the two opposing flaps directly contact one another in the resting state.

Example 32b

The valve of example 22b wherein the resilient material includes silicone.

Example 33b

The valve according to any of examples 21b-24b wherein the one-way valve includes a monolithic portion configured to simultaneously seal the channel, the first pressure relief port, and the second pressure relief port.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a side of a substrate is the "top" surface of that substrate; the substrate may actually be in any orientation so that a "top" side of a substrate may be lower than the "bottom" side in a standard terrestrial frame of reference and still fall within the meaning of the term "top." The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. A valve comprising:
   a valve body having a duckbill valve and a main valve channel, the main valve channel including a valve inlet, a valve outlet, an upstream channel portion between the valve inlet and the duckbill valve, and a downstream channel portion between the duckbill valve and the valve outlet;
   a first pressure relief port providing a fluid path from the upstream channel portion to atmosphere outside the valve body; and
   a second pressure relief port providing a fluid path from the downstream channel portion to the atmosphere outside the valve body;
   wherein in a closed configuration the duckbill valve includes a monolithic portion that simultaneously closes the channel, the first pressure relief port, and the second relief port.

2. The valve of claim 1 comprising a filter that covers the first pressure relief port.

3. The valve of claim 2 wherein the duckbill valve includes a resilient material.

4. The valve of claim 3 wherein the filter does not cover the second pressure relief port.

5. The valve of claim 4 comprising a filter medium and a cover, wherein:
the filter medium is between the first pressure relief port and the cover;
the filter medium is included in the filter;
the cover is included in an outermost surface of the valve.

6. The valve of claim 4 wherein
the valve inlet input isin configured to be upstream of the valve outlet output.

7. The valve of claim 4 wherein:
the channel includes a channel long axis that intersects the valve inlet and the valve outlet;
an additional axis is orthogonal to the channel long axis;
the monolithic portion intersects the additional axis at least four times.

8. The valve of claim 7 wherein the additional axis intersects the second pressure relief port.

9. The valve of claim 1, wherein:
the duckbill valve includes two opposing flaps;
the two opposing flaps are biased towards one another in a resting state;
the two opposing flaps directly contact one another in the resting state.

10. A valve comprising:
a housing including a channel having upstream and downstream channel portions that couple a valve input to a valve output;
a duckbill valve included within the channel and between the upstream and downstream channel portions;
a first pressure relief port providing a first fluid path from the upstream channel portion to atmosphere outside the housing; and
a second pressure relief port providing a second fluid path from the downstream channel portion to the atmosphere outside the housing;
a filter covering the first pressure relief port;
wherein in a closed configuration the duckbill valve includes a monolithic portion that simultaneously closes the channel, the first pressure fluid path, and the second fluid path;
wherein in a first open configuration the monolithic portion opens the first fluid path but closes the second fluid path;
wherein in a second open configuration the monolithic portion closes the first fluid path but opens the second fluid path;
wherein the filter is configured such that the filter filters air that passes through the first pressure relief port from the atmosphere outside the housing.

11. The valve of claim 10 wherein the duckbill valve includes a resilient material.

12. The valve of claim 11 wherein the filter does not cover the second pressure relief port.

13. The valve of claim 12 comprising a filter medium and a cover, wherein:
the filter medium is between the first pressure relief port and the cover;
the filter medium is included in the filter;
the cover is included in an outermost surface of the valve.

14. The valve of claim 12 wherein:
the channel includes a channel long axis that intersects the valve input and the valve output;
the first pressure relief port includes a first pressure relief port long axis that is parallel to the channel long axis.

15. The valve of claim 12 wherein:
the channel includes a channel long axis that intersects the valve input and the valve output;
an additional axis is orthogonal to the channel long axis;
the duckbill valve intersects the additional axis at least four times.

16. The valve of claim 15 wherein the additional axis intersects the second pressure relief port.

* * * * *

UNITED STATES PATENT AND TRADEMARK OFFICE
CERTIFICATE OF CORRECTION

PATENT NO. : 11,662,034 B2
APPLICATION NO. : 16/936963
DATED : May 30, 2023
INVENTOR(S) : Jeff J. Albertsen and Kenneth A. Jones It is certified that error appears in the above-identified patent and that said Letters Patent is hereby corrected as shown below:

In the Claims

Column 17, Line 8, In Claim 6, "the valve inlet input isin configured to be upstream of the valve outlet output." should be --the valve inlet is upstream of the valve outlet.--

Signed and Sealed this
Twenty-seventh Day of June, 2023

Katherine Kelly Vidal
*Director of the United States Patent and Trademark Office*